United States Patent [19]

Stojkovic, Ljubinko

[11] 4,238,478
[45] Dec. 9, 1980

[54] HETEROVACCINE AGAINST THE TRICHOMONAS SYNDROME, AND PROCESS FOR ITS PREPARATION

[76] Inventor: Ljubinko Stojkovic, Oberwilerstrasse 64, CH-4054 Basel, Switzerland

[21] Appl. No.: 26,496

[22] Filed: Apr. 3, 1979

Related U.S. Application Data

[63] Continuation-in-part of Ser. No. 967,033, Dec. 6, 1978, abandoned.

[30] Foreign Application Priority Data

Dec. 23, 1977 [CH] Switzerland ................. 16012/77

[51] Int. Cl.³ .................................. A61K 39/02
[52] U.S. Cl. ................................................ 424/92
[58] Field of Search .................. 424/92, 93; 195/80

[56] References Cited

U.S. PATENT DOCUMENTS

| 3,639,566 | 2/1972 | Naito et al. | 424/93 |
| 3,957,974 | 5/1976 | Hata | 424/93 |

FOREIGN PATENT DOCUMENTS

| 2946M | 8/1963 | France | 424/93 |
| 52-18879 | 2/1977 | Japan | 424/93 |
| 52-102419 | 8/1977 | Japan | 424/93 |
| 52-154590 | 12/1977 | Japan | 424/93 |
| 25675 | of 1909 | United Kingdom | 424/93 |

*Primary Examiner*—Shep K. Rose
*Attorney, Agent, or Firm*—Ladas & Parry

[57] ABSTRACT

The vaccine consists of inactivated micro-organisms of certain strains of *Lactobacterium acidophilum* (which have been deposited in a culture collection) in a physiologically tolerated solution. The micro-organisms, preferably of eight strains, are present in approximately equal numbers per strain; they are obtained by aerobic culture. The vaccine produces immunity and may be used for the therapeutic treatment of the Trichomonas syndrome.

10 Claims, No Drawings

HETEROVACCINE AGAINST THE TRICHOMONAS SYNDROME, AND PROCESS FOR ITS PREPARATION

This application is a continuation-in-part of prior application Ser. No. 967,033 filed Dec. 6, 1978, now abandoned. The benefit of the filing date of this prior application Ser. No. 967,033 is hereby claimed.

The present invention relates to a novel heterovaccine which is valuable for the therapeutic treatment of the Trichomonas syndrome, to a process for its preparation and to its use.

The genus *Trichomonas vaginalis* belongs to the protozoa and, according to the systematic classification of the protozoa which are of importance in human medicine, to the class of the Mastigophora or Flagellata. It is a basically pathogenic parasite, which is found in the female and male urogenital tract. It is mainly transmitted by cohabitation, but infections via articles have also been demonstrated.

Though men are as frequently exposed to the infection as are women, men show clinical symptoms substantially less frequently; the majority of Trichomonas carriers are free from complaints and pay no attention to a slight secretion, a symptom of urethritis.

For women, the practical significance of the infection resides, first of all, in complaints of the genital organs as a result of massive purulent inflammations of the vagina, often having critical effects on a normal marriage. The infection in general does not remain confined to the vagina and the accompanying pathogenic mixed flora is in most cases carried into the upper genital tract by the trichomonads and leads to inflammations of the appendages of the uterus (adnexitis), which are accompanied by the risk of tubar pregnancy or of blockage of the Fallopian tubes (sterility). Both the chronic infection and recurrent lapses cause substantial inflammation of the portio vaginalis uteri and of the cervix; the consequences of this are local tissue changes which range from reversible dysplasia to the preliminary stages of cervical carcinoma. The complex clinical pattern is described, overall, as the Trichomonas syndrome.

Though the preparation metronidazole [1-(2-hydroxyethyl)-2-methyl-5-nitroimidazole] is entirely suitable for destroying *Trichomonas vaginalis* and has been introduced into therapeutic practice for this indication, the number of cases nevertheless shows no decrease but, if anything, a tendency to increase; depending on the country, between 3.5 and 88% of the population are alleged to suffer from the infection, so that it has reached the proportions of a disease disseminated throughout the population.

The spread of the infection, and the repeatedly observed re-infection, are greatly enhanced by the increase in promiscuity. In addition, the obstinacy of the infection, and a certain resistance to therapy, are assisted by the constantly extending regular use of ovulation-inhibiting steroids, since it is known that all hypoovarial conditions, that is to say a relative lack of overial hormones produced by the body, inhibit epithelial proliferation in the vagina.

It has now been found that amongst the large number of naturally occurring strains (currently about 4,000 different strains are known) of *Lactobacterium acidophilum*, also referred to as *Lactobacillus acidophilus*, lactic acid bacterium, lactobacterium, lactic acid rhabdobacillus, Döderlein's rhabdobacillus or Döderlein's bacterium, there are some from which a heterovaccine valuable for the treatment of the Trichomonas syndrome can be prepared.

The individual strains were taken in hospital in 1976 from the vagina of women suffering from this syndrome. The strains were deposited on Oct. 17, 1977, in the lyophilised state, at the "Centraalbureau voor Schimmelcultures" in Baarn (Netherlands) under references CBS 465.77 to CBS 472.77 (eight individual strains).

In morphological respects, the various strains differ, inter alia, in respect of the size of the colonies formed: some colonies are very small, transparent and circular, whilst other colonies are larger and have the shape of a rosette with a furrowed surface. According to microscopic examination, all eight bacterial strains belong to the gram-positive polymorphous bacilli, which occur in the form of chains or palisades.

The biological behaviour of the strains can be characterised as follows in terms of their growth on various sources of carbon:

Table 1

| Source of carbon: | *Lactobacterium acidophilum*, Strain CBS No.: | | | | | | | |
|---|---|---|---|---|---|---|---|---|
| | 465.77 | 466.77 | 467.77 | 468.77 | 469.77 | 470.77 | 471.77 | 472.77 |
| Arabinose | − | + | + | + | + | − | − | ± |
| Cellobiose | + | − | − | − | − | − | − | − |
| Lactose | + | + | + | + | + | − | − | + |
| Maltose | + | + | + | + | + | ± | + | + |
| Mannitol | − | + | + | + | + | + | − | − |
| Melibiose | + | + | + | − | + | − | + | − |
| Raffinose | + | + | + | − | + | − | + | − |
| Rhamnose | + | + | + | + | + | + | − | + |
| Salicin | + | + | + | + | + | + | − | + |
| Sucrose | + | + | + | + | + | + | + | + |
| Trehalose | + | + | + | + | + | + | − | − |
| Xylose | ± | − | − | − | − | ± | − | − |
| Ribose | + | + | + | + | + | + | − | + |
| Starch | ± | − | − | − | − | ± | − | − |

The strains CBS 466.77, 467.77 and 469.77 show identical biochemical or fermentative properties.

The heterovaccine according to the invention thus consists of inactivated micro-organisms of strains of *Lactobacterium acidophilum* mentioned above in a physiologically tolerated solution, the micro-organisms present being from some or all of these strains and being present in approximately equal numbers per strain. There should be micro-organisms of at least 3 strains in the vaccine.

A heterovaccine according to the invention may be prepared by a process wherein some or all of the abovementioned strains of *Lactobacterium acidophilum* are cultured individually on a liquid nutrient medium under aerobic conditions, after termination of the culturing the biological material formed is separated off and inactivated and the inactivated micro-organisms obtained from the individual strains are mixed with one another, in a physiologically tolerated solution, in amounts which are approximately inversely proportional to the density of the culture (number of micro-organisms per ml of culture liquid) determined after termination of the culture or after inactivation.

The strains mentioned are selected so that in carrying out the process using all eight strains, a universally effective vaccine is obtained. This term means a vaccine which is effective in virtually all female patients, or a vaccine by means of which the Trichomonas syndrome can be treated successfully regardless of the origin of the infection. Hence the vaccine in which inactivated micro-organisms of the eight strains mentioned are present is the preferred form of the invention, and the preparation of the vaccine using the eight strains mentioned is the most preferred embodiment of the process. However, it is possible to use less than the eight strains, e.g. 7, 6, 5, 4 or even 3, and still obtain results which are worthwhile even if not as good in all circumstances as a vaccine from all eight strains.

Various liquid nutrient media customary in microbiology can be used for culturing the strains. A nutrient medium of the following composition has proved particularly advantageous:

| | |
|---|---|
| Tryptose peptone | 5 g |
| Casein hydrolysate | 8 g |
| Meat extract | 10 g |
| Yeast dialysate | 100 ml |
| $K_2HPO_4$ | 2 g |
| Triammonium citrate | 2 g |
| Sodium acetate | 5 g |
| Salt mixture | 5 ml |
| Polyoxyethynene derivatives of sorbitan oleates (Tween 80 $^R$) | 1 ml |
| Glucose | 10 g |
| Lactose | 10 g |
| Distilled water to make up to | 1,000 ml |

The above mentioned salt mixture consists of:

| | |
|---|---|
| $MgSO_4 \cdot 7H_2O$ | 11.5 g |
| $MnSO_4 \cdot 2H_2O$ | 2.4 g |
| $FeSO_4 \cdot 7H_2O$ | 0.68 g |
| Distilled water to make up to | 100 ml |

The liquid medium is brought to a pH value of 6.1–6.8, preferably about 6.5, and is sterilised for 20 minutes in an autoclave at a temperature of 115° C.

The nutrient medium may then be divided amongst sterilised vessels, for example Erlenmeyer flasks, and the content of each vessel inoculated with a sample of the individual strain. The culture is advantageously effected at a temperature of 32° to 45° C., preferably at about 37° C., for example for 48 hours. After this time, or when an amount of biological material sufficient for the intended vaccine production has formed, the biological material may be collected under sterile conditions and freed from adhering nutrient medium by centrifuging; for example, the material may be centrifuged for 1 hour at 3,000 revolutions/minute.

The sediment, consisting of the biological material, may then be re-suspended, preferably in physiological sodium chloride solution, and may thereafter by inactivated by a conventional method. A treatment with formaldehyde and phenol is very particularly suitable for the inactivation. A concentration of the suspension of 0.3% by weight in respect of formaldehyde and 0.5% by weight in respect of phenol, and a treatment time of from 3 to 5 days, prove to be advantageous. After the inactivation, the suspension may again be centrifuged, for example for 1 hour at 3,000 revolutions/minute, in order to free the inactivated material from the agent used for inactivation, or from the excess of formaldehyde and phenol.

The material obtained from each individual strain may be re-suspended, preferably in physiological sodium chloride solution, and tested for sterility, and for the presence of any still viable lactobacteria, in accordance with the methods described later. If both tests prove negative, that is to say if the material is suitable for the preparation of the vaccine, the density of the culture, or the number of micro-organisms per ml of culture liquid, reached with each strain is determined.

If for any reason it is not possible to mix the individual biological materials immediately after inactivation, the corresponding suspensions may in the interim by stored at a temperature of about 4° C. It is also possible to lyophilise the inactivated micro-organisms of each individual strain and store them in this state at about 4° C. The lyophilised strains can be stored unchanged at this temperature for a period of at least three years. A suitable protective colloid for the lyophilisation is in particular a medium containing by weight 5.6% of gelatine, 37.5% of sucrose and 0.5% of calcium lactobionate; advantageously, the lyophilisation is carried out for 24 hours.

Finally, the materials which have been obtained from each of the individual strains and have been inactivated are mixed in such amount that a vaccine which contains approximately the same number of micro-organisms of each strain per ml is produced. The vaccine obtained is advantageously diluted with physiological sodium chloride solution to the point where it contains about $14 \times 10^9$ micro-organisms per ml.

The vaccine usually has a total nitrogen content (determined by the Kjeldahl method) of 3.68 mg%, based on the dry material. It has proved advantageous to add a preservative, for example formaldehyde or phenol (the concentration of formaldehyde or phenol being, for example, 0.25% by weight) or sodium ethyl-mercurithiosalicylate (Thiomersal) and to allow the vaccine to ripen for about 30 days at a temperature of 4° C. before packing it in ampoules. Preferably, each ampoule contains 0.5 ml of the vaccine which has been described. Of course, these last measures should also be carried out under sterile conditions and in pyrogen-free glass equipment.

The ampoule contents can also be lyophilised and stored, up to the time of use, in the form of a dry ampoule, preferably at about 4° C. The shelf life of the vaccine, whether in the form of the conventional ampoules or of dry ampoules, is at least three years from the time of preparation, if the vaccine is stored at a temperature of 2° to 8° C. (normal refrigerator temperature); if stored at about 20° C., the vaccine can be kept for about 6 months. It should also be mentioned that a period of three years is the maximum use period permitted by the World Health Organisation for an inactivated vaccine (dead vaccine).

The following tests should be carried out on the vaccine before it is released for therapeutic use:

1. Test for sterility (1st sterility test)
2. Test for toxicity
3. Test for antigen action
4. Test for the presence of remaining viable lactobacteria (2nd sterility test).

These tests are preferably carried out in accordance with the instructions of the World Health Organisation (Requirements for Biological Substances, Technical Reports of the WHO No. 323, 1966) and of the European Pharmacopoeia II, (1971).

To test for sterility, 1 ml portions of vaccine were introduced into test tubes containing thioglycollate nutrient medium and into test tubes containing Sabouraud's bouillon, after which the test tubes were incubated for 10 days at a temperature of 37° C., and a corresponding series of identically treated test tubes was also incubated for the same period at a temperature of 25° C. It was found that all test tubes in both series had remained sterile.

The toxicity test was carried out on guinea pigs and on white mice. 5 ml of vaccine (ie. 10 times more than the individual dose envisaged for human patients) were administered intramuscularly to each of five guinea pigs having an average body weight of 300 g, 2.5 ml being introduced into each hind leg; after a period of observation of 14 days, the health of the five animals continued unchanged and furthermore no reactions were found in the treated legs. In addition, each of ten white mice having an average body weight of 20 g was given 0.5 ml of vaccine administered intramuscularly into a hind leg; after a period of observation of 14 days, the health of the ten mice continued unchanged.

The antigen action was first tested in vivo on guinea pigs. Of the animals mentioned in the preceding paragraph, three animals were each treated intracardially with 1 ml of vaccine after 14 days; in spite of the relatively high dose, no anaphylactic reaction was observed. Thereafter, the vaccine was also tested in vitro, by the Ouchterlony immunodiffusion method, against samples of normal human serum; no positive reaction was found.

To test for the presence of remaining viable lactobacteria, samples of the vaccine were cultured on a solid nutrient medium suitable for isolating and identifying these micro-organisms. A nutrient medium of the following composition is suitable for the purpose:

| | |
|---|---|
| Water | 800 ml |
| Tripcasein | 16 g |
| Solution 1 | 50 ml |
| Solution 2 | 10 ml |
| Solution 3 | 10 ml |
| Solution 4 | 10 ml |
| Fresh yeast | 100 g |
| Witte peptone | 10 g |
| Soluble starch, 0.5% by weight (in the form of a solution) | 5 g |
| Water to make up to | 1,000 ml |

The abovementioned solutions, which were all aqueous solutions, have the following composition, by weight:
Solution 1: contains 10% of NaCl
Solution 2: contains 2% of KCl and 5% of $Na_2CO_3$
Solution 3: contains 2% of $CaCl_2$ and 1% of $MgCl_2$
Solution 4: contains 2.5% of $K_2HPO_4$ 25 g of agar-agar are added to the resulting final solution, the pH value is adjusted to 5.5–6.7, preferably to about 6.0, and the medium is sterilised for 20 minutes in an autoclave at a temperature of 115° C. Thereafter, a solution of 3 g of maltose, 10 g of glucose and 10 g of lactose in 100 ml of water, is added, followed by 30 ml of a 1% by weight cystein hydrochloride solution. Each of these solutions is first sterilised by sterile filtration, for example through a $G_5$ glass filter. Finally, 10% by weight of defibrinated human blood are also added to this medium. The blood agar nutrient medium thus prepared is inoculated with samples of the vaccine and is incubated at a temperature of 37° C. As a control, samples of *Lactobacterium acidophilum* are used for inoculation, and cultured, under the same conditions.

In these tests, no viable micro-organisms were detectable in the vaccine, which proves the complete inactivation by the preferred method, which employed formaldehyde and phenol. Accordingly, the vaccine according to the invention is a so-called dead vaccine. Since on the other hand it displays an action against an infection, and its secondary phenomena, caused by a different type of micro-organism, namely *Trichomonas vaginalis*, the vaccine belongs to the category of the heterovaccines.

The vaccine inter alia causes the formation of specific antibodies against *Lactobacterium acidophilum*, especially against its abnormal and polymorphic forms, which are partially responsible for the pathological change in the pH value of the vagina in the case of the Trichomonas syndrome. This immunising action can be demonstrated both in animal experiments and in clinical tests, as described below.

In animal experiments, two rabbits respectively weighing 2,950 and 3,200 g were used and were inoculated intravenously twice, at an interval of two weeks, with 0.5 ml of vaccine each time. One month after the second treatment, blood was taken from the animals and the serum isolated therefrom. If antibodies have formed, the serum should, in a dilution of at least 1:50, specifically cause the agglutination of the lactobacteria of those strains from which the vaccine was prepared; in that case, the serum exhibits a positive titre of agglutinins at the dilution investigated. In the case of the first and second rabbit, the titre of agglutinins before inoculation was negative, at a serum dilution of 1:10 in each case; one month after the second treatment it was positive at a dilution of 1:160 and 1:80 respectively.

The new vaccine permits curative and prophylactic treatment of the Trichomonas syndrome and of acute, chronic and asymptomatic trichomoniasis. Whether used curatively or prophylactically, the following posology is recommended: administration of a dose of 0.5 ml (that is to say about $7 \times 10^9$ micro-organisms) intramuscularly three times, at successive intervals of 2 weeks, followed by a booster injection of the same dose (0.5 ml) one year after the start of the treatment.

Clinical tests were carried out in accordance with the above posology, and in these serological investigations were carried out on blood from 97 female patients. The blood was taken from the patients in accordance with a fixed time schedule and the isolated blood serum was tested for the presence of lactobacteria antibodies. For this purpose, the serum, in geometrically increasing dilution (from 1:10 to 1:1,280) was treated with an antigen or agglutinogen corresponding to the vaccine and any agglutination which took place was observed. The agglutinogen used was a freshly prepared, that is to say less than three months old, suspension of inactivated micro-organisms of *Lactobacterium acidophilum* of the same strains, in the same ratio and at the same concentration ($14 \times 10^9$ micro-organisms per ml) as the vaccine itself; phenol, in a concentration of 0.25% of the suspension, was used for the inactivation. The occurrence, and the development with time, of the agglutinins in the serum as a consequence of the inoculation can be seen clearly from the titre values given in the table which follows.

Table 2

Distribution of the agglutinin titre before and after inoculation

| Titre | Before inoculation | 2 weeks after the 3rd injection | 3 months | 6 months | 12 months after the start of the inoculation |
|---|---|---|---|---|---|
| <1:10 | 16 | 1 | 1 | 1 | 1 |
| 1:10 | 0 | 0 | 0 | 0 | 1 |
| 1:20 | 8 | 2 | 3 | 3 | 3 |
| 1:40 | 13 | 0 | 1 | 3 | 8 |
| 1:80 | 29 | 3 | 5 | 6 | 17 |
| 1:160 | 18 | 13 | 11 | 16 | 16 |
| 1:320 | 13 | 49 | 48 | 40 | 15 |
| 1:640 | 0 | 25 | 24 | 20 | 3 |
| 1:1,280 | 0 | 4 | 3 | 3 | 0 |
| Total* | 97 | 97 | 96 | 92 | 64 |
| Geometrical mean value of the titre | 1:56.4 | 1:356 | 1:293 | 1:257 | 1:120 |

*The decrease in the total number after 3, 6 and 12 months results from certain patients no longer coming back for a check.

From the geometrical mean values of the titre given above it is possible to calculate, for example, that 2 weeks after conclusion of the inoculation the titre has increased by an average factor of 6.3. One year after the start of the inoculation, that is to say at the time of the booster injection, the agglutinin titre is still 2.1 times greater than before, which can partially explain the long-lasting success of the inoculation.

If the increase in titre during the period immediately following the inoculation, that is to say in the period between the taking of the first and of the second blood sample, is examined, it is found to show the following distribution in respect of the number of patients.

Table 3

| Increase factor | Increase in agglutinin titre | | | | | |
|---|---|---|---|---|---|---|
| | 2× | 4× | 8× | 16× | 32× | 64× and more |
| Number of patients | 13 | 13 | 21 | 10 | 6 | 7 |
| Proportion of the total number of patients | 13.4% | 13.4% | 21.6% | 10.3% | 6.2% | 7.2% |

The following summarising clinical report gives a picture of the success of the treatment. 200 women varying in age from 15 to 59 years and suffering from the Trichomonas syndrome were treated, as outpatients, with the vaccine (prepared from the eight strains mentioned); the checks extended over a period of, in some cases, more than 2 years (2 patients no longer presented themselves for check-up). 138 patients, that is to say 69% of the total, had previously been treated repeatedly with oral or vaginal preparations, especially metronidazole, but without long-term success, because of re-infection. Before starting the treatment, a gynaecological investigation, including colposcopy and Papanicolaou smear, was carried out in addition to blood and urine tests; in addition, smears were taken from the vulva, the vagina, the cervix and the urethra and from these a natural preparation, as well as a Bramstained and a Giemsa-stained preparation were prepared, and a *Trichomonas vaginalis* culture was set up. All these investigations were repeated 6 weeks, 4 months and 12 months after the start of the treatment.

Before starting the therapy, 145 of the 200 female patients (72.5%) showed pronounced symptoms of the Trichomonas syndrome, with severe colpitis, pruritus, copious greenish-yellow, foul-smelling vaginal discharge, dyspareunia, dysuria and the like; the colposcopy showed oedema and reddening of the epithelium of the vagina and of the vaginal portion of the cervix. In addition, 61 patients showed crythroplasia of the vaginal portion of the cervix, and 13 others showed chronic cervicitis. In the remaining 55 patients (27.5%) the symptoms were less obvious—slight colpitis.

The treatment was carried out in accordance with the posology given above. In the cases of slight colpitis, no additional therapy was used; to alleviate acute symptoms, antibiotics were applied locally and in the case of severe conditions a preparation of micro-organisms consisting of strains of *Lactobacterium acidophilum* effective against Moniliasis was also applied locally. However, in no case was metronidazole or a similar nitroimidazole derivative administered.

If the vaginal secretion is grouped under the following classes in accordance with Jirovec [W. Ritzerfeld, Der Gynäkologe 2 (1), pages 2–6 (1969[, the success of the treatment can be seen clearly from Table 4.
Class I: as in healthy women
Class II: non-purulent bacterial discharge
Class III: purulent bacterial discharge
(Class IV: gonorrhoea—no cases included in the present investigation)
Class V: trichomoniasis (positive natural preparation)
Class VI: vaginal mycosis (*Candida albicans*)

Table 4

| Time of examination | Number | Class II | Class III | Class V | Class VI |
|---|---|---|---|---|---|
| Before start of inoculation | 200 | — | — | 194 97% | 6 3% |
| 2 weeks after 3rd injection | 200 | 139 69.5% | 47 23.5% | 14 7% | — |
| 3 months after 3rd injection | 198 | 164 82% | 27 13.5% | 9 4.5% | — |
| 12 months after start of inoculation | 198 | 157 79.3% | 32 16.2% | 9 4.5% | — |

The 9 patients in which *Trichomonas vaginalis* was still microscopically detectable at the second check-up, three months after conclusion of the inoculation, remained refractory to therapy; even a peroral treatment with a trichomonacide did not in any way change this situation. Furthermore, even after 12 months, cervical changes in the form of chronic cervicitis or massive erythroplasia, remained. Perhaps these failures are attributable to the fact that these women were incapable of sufficient generation of antibodies, in spite of correct inoculation.

Of 198 treated patients, 189 (95.5%) exhibited, after 12 months, a vaginal secretion of Class II and III, that is to say they had been cured as far as their trichomoniasis was concerned. This proportion of cures was achieved in 55 patients with slight colpitis without any additional therapy. The patients have continued under observation, in some cases for what is now more than 2 years; during this time, no relapses or re-infections have occurred, which is a new achievement in this field of medicine and would appear to indicate the regeneration of a stable vaginal medium hostile to trichomonads. Finally, the vaccine appears also to have a beneficial effect on cervical changes and on lesions of the cervical portion of the vagina. The overall result is even more striking if it is borne in mind that the majority of the patients had already been treated locally and systemically with various chemical compounds, but only with transient success.

Apart from an occasional reddening or slight swelling in the region of the point of injection, undesirable sideeffects did not occur in any of the patients, during treatment or immediately thereafter. Furthermore, no allergic or toxic reactions were found.

The inoculation should not be employed in cases of acute febrile infections, diseases of the hematopoietic system or severe kidney insufficiency.

Simultaneous treatment of the partners of the women treated with the vaccine is admittedly desirable but is not absolutely essential from the point of view of the female patient since she becomes immune as a result of the inoculation.

I claim:

1. A heterovaccine for the therapeutic treatment of the Trichomonas syndrome, consisting essentially of inactivated micro-organisms of strains of *Lactobacterium acidophilum*, which have been deposited with the "Centraalbureau voor Schimmelcultures" in Baarn (Netherlands) under references CBS 465.77, CBS 466.77, CBS 467.77, CBS 468.77, CBS 469.77, CBS 470.77, CBS 471.77 and CBS 472.77, in a physiologically tolerated solution, the micro-organisms present being from at least three of the above strains and being present in approximately equal numbers per strain.

2. A heterovaccine according to claim 1, wherein the inactivated micro-organisms present are from all eight of the deposited strains.

3. A heterovaccine according to claim 1 or 2, containing about $14 \times 10^9$ inactivated micro-organisms per ml.

4. A heterovaccine according to claim 1 or 2, additionally containing a preservative.

5. A process for the preparation of a heterovaccine according to claim 1, wherein at least three of the strains of *Lactobacterium acidophilum* which have been deposited with the "Centraalbureau voor Schimmelcultures" in Baarn (Netherlands) under references CBS 465.77, CBS 466.77, CBS 467.77, CBS 468.77, CBS 469.77, CBS 470.77, CBS 471.77 and CBS 472.77 are cultured individually on a liquid nutrient medium under aerobic conditions, after termination of the culturing the biological material formed is separated off and inactivated and the inactivated micro-organisms obtained from the individual strains are mixed with one another, in a physiologically tolerated solution, in amounts which are approximately inversely proportional to the density of the culture (number of micro-organisms per ml of culture liquid) determined after termination of the culturing or after inactivation.

6. A process according to claim 5, wherein all eight of the deposited strains are used.

7. A process according to claim 5 or 6, wherein the culture is effected at a pH value of 6.1 to 6.8 and at a temperature of 32° to 45° C.

8. A process according to claim 5 or 6, wherein the inactivation of the biological material formed by the culturing is effected by treatment with formaldehyde and phenol.

9. A process according to claim 5 or 6, wherein the inactivated micro-organisms are added to the physiologically tolerated solution in such amount, or the vaccine obtained is diluted with the physiologically tolerated solution to such an extent, that about $14 \times 10^9$ inactivated micro-organisms are present per ml.

10. A method of treating Trichomonas syndrome which comprises administering the heterovaccine according to claim 1 or 2 to women suffering from said syndrome at a dose of 0.5 ml intramuscularly three times at successive intervals of 2 weeks, followed by a booster injection of 0.5 ml one year after the start of the treatment.

* * * * *